United States Patent
Zhong et al.

(10) Patent No.: US 11,318,135 B2
(45) Date of Patent: *May 3, 2022

(54) USE OF FAVIPIRAVIR IN TREATMENT OF CORONAVIRUS INFECTION

(71) Applicant: Academy of Military Medical Sciences, Beijing (CN)

(72) Inventors: Wu Zhong, Beijing (CN); Ruiyuan Cao, Beijing (CN); Cheng Cao, Beijing (CN); Ting Gao, Beijing (CN); Gengfu Xiao, Beijing (CN); Zhihong Hu, Beijing (CN); Manli Wang, Beijing (CN); Leike Zhang, Beijing (CN); Song Li, Beijing (CN)

(73) Assignee: Academy of Military Medical Sciences, Beijing (CN)

( * ) Notice: Subject to any disclaimer, the term of this patent is extended or adjusted under 35 U.S.C. 154(b) by 0 days.

This patent is subject to a terminal disclaimer.

(21) Appl. No.: 17/378,361

(22) Filed: Jul. 16, 2021

(65) Prior Publication Data

US 2021/0346376 A1 Nov. 11, 2021

Related U.S. Application Data

(63) Continuation of application No. 17/070,620, filed on Oct. 14, 2020.

(30) Foreign Application Priority Data

Jan. 21, 2020 (CN) .......................... 202010070142.0

(51) Int. Cl.
*A61K 31/4965* (2006.01)
*A61P 31/14* (2006.01)

(52) U.S. Cl.
CPC .......... *A61K 31/4965* (2013.01); *A61P 31/14* (2018.01)

(58) Field of Classification Search
CPC ................................................. A61K 31/4965
USPC ................................................... 514/255.06
See application file for complete search history.

(56) References Cited

U.S. PATENT DOCUMENTS

| | | |
|---|---|---|
| 2003/0130213 A1 | 7/2003 | Egawa et al. |
| 2012/0010221 A1 | 1/2012 | Kakuda et al. |
| 2015/0196578 A1 | 7/2015 | Guilford et al. |
| 2018/0207145 A1 | 7/2018 | Washburn |
| 2021/0220353 A1 | 7/2021 | Zhong et al. |
| 2021/0220377 A1 | 7/2021 | Zhong et al. |

FOREIGN PATENT DOCUMENTS

| | | |
|---|---|---|
| CN | 1418220 A | 2/2001 |
| CN | 102655859 A | 9/2012 |
| CN | 107072976 A | 8/2017 |
| CN | 107737128 A | 2/2018 |
| CN | 111265528 A | 6/2020 |
| CN | 111557939 A | 8/2020 |
| RU | 2527766 C2 | 9/2014 |
| TW | 201402556 A | 1/2014 |
| TW | 201402556 A | 1/2014 |
| WO | WO 2011047048 A1 | 4/2011 |
| WO | WO 2013/180149 A1 | 12/2013 |
| WO | WO 2015/173701 A2 | 11/2015 |
| WO | WO 2020/202111 A1 | 10/2020 |
| WO | WO 2021/001458 A1 | 1/2021 |
| WO | WO 2021007283 A1 | 1/2021 |
| WO | WO 2021/038296 A2 | 4/2021 |

OTHER PUBLICATIONS

Jordan, Antiviral Chemistry and Chemotherapy 2018, vol. 26: 1-19.*

Du, Clinical Pharmacology & Therapeutics | vol. 108 No. 2 | Aug. 2020.*

Agostini, M. L., et al., "Coronavirus Susceptibility to the Antiviral Remdesivir (GS-5734) Is Mediated by the Viral Polymerase and the Proofreading Exoribonuclease," mBio 9(2):e00221-18, 15 pages, American Society of Microbiology, United States (Mar. 2018).

Agostini, M. L., et al., "Small-Molecule Antiviral β-D-$N^4$-Hydroxycytidine Inhibits a Proofreading-Intact Coronavirus with a High Genetic Barrier to Resistance," Journal of Virology 93(24):e01348-19, 14 pages, American Society for Microbiology, United States (Dec. 2019).

Barnard, D. L., et al., "Inhibition of severe acute respiratory syndrome-associated coronavirus (SARSCoV) by calpain inhibitors and beta-D-$N^4$-hydroxycytidine," Antiviral Chemistry & Chemotherapy 15(1): 15-22, SAGE Publications Inc., United Kingdom (Jan. 2004).

Brown, A. J., et al., "Broad spectrum antiviral remdesivir inhibits human endemic and zoonotic deltacoronaviruses with a highly divergent RNA dependent RNA polymerase," Antiviral Research 169:104541, Elsevier BV, Netherlands (Sep. 2019).

Furuta, Y., et al., "Mechanism of action of T-705 against influenza virus," Antimicrobial Agents and Chemotherapy 49(3):981-986, American Society for Microbiology, United States (Mar. 2005).

(Continued)

*Primary Examiner* — Nizal S Chandrakumar
(74) *Attorney, Agent, or Firm* — Sterne, Kessler, Goldstein & Fox P.L.L.C.

(57) ABSTRACT

The present application relates to a Favipiravir compound represented by Formula I, a geometric isomer, a pharmaceutically acceptable salt, a solvate and/or a hydrate thereof, and a pharmaceutical composition comprising the compound for treating a coronavirus infection.

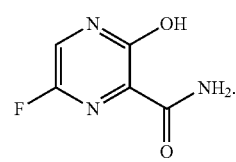

I

16 Claims, 1 Drawing Sheet

Specification includes a Sequence Listing.

(56) References Cited

OTHER PUBLICATIONS

Furuta, Y., et al., "Favipiravir (T-705), a broad spectrum inhibitor of viral RNA polymerase," Proc Jpn Acad Ser B Phys Biol Sci 93(7):449-463, The Japan Academy, Japan (2017).
Genbank, "Severe acute respiratory syndrome coronavirus 2 isolate Wuhan-Hu-1, complete genome," ncbi.nlm.nih.gov, Accession No. NC_045512.2, accessed at URL:[https://www.ncbi.nlm.nih.gov/nuccore/NC_045512] on May 31, 2021, 16 pages.
Sheahan, T. P., et al., "Broad-spectrum antiviral GS-5734 inhibits both epidemic and zoonotic coronaviruses," Science Translational Medicine 9(396):eaal3653, 10 pages, American Association for the Advancement of Science, United States (Jun. 2017).
Tsai, C-H., et al., "Antiviral therapy targeting viral polymerase," Current Pharmaceutical Design 12(11):1339-1355, 18 pages, Bentham Science Publishers Ltd., United Arab Emirates (2006).
World Health Organization, "Novel Coronavirus—Thailand (ex-China)," accessed at URL:[https://www.who.int/emergencies/disease-outbreak-news/item/2020-DON234] on Jul. 7, 2021, 3 pages (Jan. 2020).
Wu, Y-S., et al., "Antiviral drug discovery against SARS-CoV," Current Medicinal Chemistry 13(17):2003-2020, Bentham Science Publishers Ltd., United Arab Emirates (2006).
International Search Report and Written Opinion for International Application No. PCT/CN2020/097395, China National Intellectual Property Administration, China, dated Oct. 20, 2020, 22 pages (with English Translation of ISR).
First Office Action for Taiwanese Patent Application No. 109135164, dated Jun. 25, 2021, Taiwan Intellectual Property Office, Taiwan, 11 pages (with English Translation).
McKimm-Breschkin, J. L., et al., "Meeting Report: Prevention and treatment of respiratory viral infections: presentations on antivirals, traditional therapies and host-directed interventions at the 5$^{th}$ ISIRV Antivirl Group conference," *Antiviral Research* 149:118-142, Elsevier, Netherlands (2018).
Furuta, Yousuke, et al. "Favipiravir (T-705), a novel viral RNA polymerase inhibitor." Antiviral research 100(2): 446-454 (2013).
Kuikui; L. et al., "Determination of the Related Substances in Favipiravir by HPLC," China Pharmacist 21(4):739-42 (2018).
Office Action for Tonga Patent Application No. TO/P/21/00045, dated May 3, 2021, The Ministry of Trade and Economic Development, Nuku'alofa, Tonga; Australian Search and Examination Report furnished for use by Tonga dated Apr. 28, 2021, 11 pages.
Delang, Leen, et al., "Favipiravir as a potential countermeasure against neglected and emerging RNA viruses." Antiviral research 153: 85-94, Elsevier, Netherlands (2018).
Cai, Qingxian, et al. "Experimental treatment with favipiravir for COVID-19: an open-label control study." Engineering 6(10): 1192-1198, Elsevier, Netherlands (2020).
McCurry, J. "Japanese flu drug "clearly effective" in treating coronavirus, says China." The Guardian 18, accessed at URL:https://www.theguardian.com/world/2020/mar/18/japanese-flu-drug-clearly-effective-in-treating-coronavirus-says-china, accessed on Mar. 29, 2021 (2020).
European Search Report for EP Application No. 20202257.0, European Patent Office, Munich, completed on Mar. 30, 2021, 11 pages.
Office Action for Chinese Patent Application No. 202010572752.0, dated Oct. 23, 2020, The State Intellectual Property Office of China, Beijing, China, 3 pages.
Jizheng; Wang "Clinical Diagnosis and Treatment of Respiratory Meidicne," in Clinical Diagnostics in Pulmonology pp. 87, Tianjin Science and Technology Press, P.R. China (2018).
Shashank, J. et al. "Role of favipiravir in the treatment of COVID-19." International Journal of Infectious Diseases, Elsevier, Netherlands (2020).
Co-pending Application, U.S. Appl. No. 17/378,415, inventors Wu Zhong et al., filed Jul. 16, 2021 (Not Published).
Office action and search report for Japanese Application No. JP 2020-173044, Japan Patent Office, Tokyo, Japan, dated Oct. 22, 2021.
World Health Organization, "COVID-19-China," accessed at URL:[https://www.who.int/emergencies/disease-outbreak-news/item/2020-DON233] on Oct. 6, 2021, 4 pages (Jan. 2020).
Anonymous, "Novel Coronavirus (2019—nCoV) Situation Report—1," World Health Organization Jan. 20, 2020, URL:[https://www.who.int/docs/default-source/coronaviruse/situation-reports/20200121- sitrep-1-2019-ncov.pdf [retrieved on Oct. 4, 2021].
Ogata, Y., et al., "Revised virus classification," Chemistry and Biological 58(1):20-30, Japan Society for Bioscience and Biotechnology, Japan (Jan. 2020).
Genbank, "Wuhan seafood market pneumonia virus isolate Wuhan-Hu-1, complete genome," ncbi.nlm.nih.gov, Accession No. NC_045512.1, accessed at URL:[https://www.ncbi.nlm.nih.gov/nuccore/NC_045512.1] on Jan. 18, 2022, 4 pages (Jan. 2020).
Wu, F., et al., "A new coronavirus associated with human respiratory disease in China," Nature 579:265-269; Extended Date Fig. 1-9; and Supplementary information 18 pages, Springer Nature, United Kingdom (Mar. 2020).
Zhang, W-F., et al., "Novel Coronavirus Polymerase and Nucleotidyl-Transferase Structures: Potential to Target New Outbreak," The Journal of Physical Chemistry Letters 11:4430-4435, American Chemical Society, United States (May 2020).
Mendenhall, M., et al., "Effective Oral Favipiravir (T-705) Therapy Initiated after the Onset of Clinical Disease in a Model of Arenavirus Hemorrhagic Fever," PLOS: Neglected Tropical Diseases 5(10):e1324, doi:10.1371/journal.pntd.0001342 (Oct. 2011).
Gowen, B.B., et al., "Efficacy of favipiravir (T-705) and T-1106 pyrazine derivatives in phlebovirus disease models," Antiviral Research 86(2):121-127; doi:10.1016/j.antiviral.2009.10.015 (May 2010).
Furuta, Y., et al., "In Vitro and In Vivo Activities of Anti-Influenza Virus Compound T-705," Antimicrobial Agents and Chemotherapy 46(4):977-981, American Society for Microbiology, United States (Apr. 2002).
Gowen, B.B., et al., "In Vitro and In Vivo Activities of T-705 against Arenavirus and Bunyavirus Infections," Antimicrobial Agents and Chemotherapy 51(9):3168-3186, American Society for Microbiology, United States (Sep. 2007).
Sleeman, K., et al., "In Vitro Antiviral Activity of Favipiravir (T-705) against Drug-Resistant Influenza and 2009 A(H1N1) Viruses," Antimicrobial Agents and Chemotherapy 54(6):2517-2524, American Society for Microbiology, United States (Jun. 2010).
Delang, L., et al., "Mutations in the chikungunya virus non-structural proteins cause resistance to favipiravir (T-705), a broad-spectrum antiviral," 69:2770-2784, British Society for Antimicrobial Chemotherapy, United Kingdom (Jun. 2014).
Wang, M., et al., "Remdesivir and chloroquine effectively inhibit the recently emerged novel coronavirus (2019-nCoV) in vitro." Cell Research 30:269-271, Springer Nature, Germany (Feb. 2020); https://doi.org/10.1038/s41422-020-0282-0.
Min, J.S., et al., "A Cell-Based Reporter Assay for Screening Inhibitors of MERS Coronavirus RNA-Dependent RNA Polymerase Activity," Journal of Clinical Medicine 9:2399 (16 pages), MDPI, Switzerland (Jul. 2020); doi:10.3390/jcm9082399.
Sheahan, T.P., et al., "Comparative therapeutic efficacy of remdesivir and combination lopinavir, ritonavir, and interferon beta against MERS-CoV," Nature Communications 11:222 (14 pages), NatureResearch, United Kingdom (Jan. 2020); https://doi.org/10.1038/541467·019·13940-6I.
Delang, L., et al., "Favipiravir as a potential countermeasure against neglected and emerging RNA viruses," Antiviral Research 153:85-94, Elsevier B.V., Netherlands (May 2018); https://doi.org/10.1016/j. antiviral.2018.03.003.
Huchting, J., et al., "Cell line-dependent activation and antiviral activity of T-1105, the non-fluorinated analogue of T-705 (favipiravir)," Antiviral Research 167:1-5, Elsevier B.V., Netherlands (Jul. 2019); https://doi.org/10.1016/j.antiviral.2019.04.002.

\* cited by examiner

```
SEQUENCE LISTING

<160> NUMBER OF SEQ ID NOS: 2

<210> SEQ ID NO 1
<211> LENGTH: 21
<212> TYPE: DNA
<213> ORGANISM: Artificial Sequence
<220> FEATURE:
<223> OTHER INFORMATION: Primer

<400> SEQUENCE: 1
caatggttta acaggcacag g                                          21

<210> SEQ ID NO 2
<211> LENGTH: 21
<212> TYPE: DNA
<213> ORGANISM: Artificial Sequence
<220> FEATURE:
<223> OTHER INFORMATION: Primer

<400> SEQUENCE: 2
ctcaagtgtc tgtggatcac g                                          21
```

USE OF FAVIPIRAVIR IN TREATMENT OF CORONAVIRUS INFECTION

The present application is based on and claims the benefit of priority from Chinese application No. 202010070142.0, filed on Jan. 21, 2020, the disclosure of which is incorporated herein by reference in its entirety.

REFERENCE TO SEQUENCE LISTING SUBMITTED ELECTRONICALLY

The content of the electronically submitted substitute sequence listing, file name 2020-10-13_SeqListing_3274-0290001.txt, size 631 bytes; and date of creation Oct. 13, 2020, filed herewith, is incorporated herein by reference in its entirety.

TECHNICAL FIELD

The present application relates to use of Favipiravir represented by the following Formula I, a geometric isomer, a pharmaceutically acceptable salt, a solvate, and/or a hydrate thereof, and a pharmaceutical composition comprising the above compound, in treating an infection caused by a coronavirus, especially SARS coronavirus (SARS-CoV) and SARS-CoV-2.

I

BACKGROUND ART

Favipiravir (compound represented by Formula I, T-705) with chemical name of 6-fluoro-3-hydroxypyrazine-2-carboxamide, which is a nucleoside analogue drug, is a viral RNA polymerase inhibitor. This drug is a broad-spectrum antiviral drug that has been approved as an anti-influenza drug in Japan.

Favipiravir has good inhibitory effects in vitro and in vivo on members of virulent RNA virus families such as Filoviridae, Bunyaviridae, Arenaviridae, Togaviridae, as well as members of other virus families such as Orthomyxoviridae, Paramyxoviridae, Picornaviridae, Flaviviridae, but its activity against coronavirus has not been reported. After entering a cell, Favipiravir can be converted into an active form of triphosphate, which is incorporated into the RNA chain during the transcription and replication of RNA virus, and non-specifically terminates the extension of the viral RNA chain, thereby achieves antiviral effects.

It has been reported that Favipiravir can effectively inhibit the virus titer in the supernatant after Vero E6 cell line was infected by viruses, and has a half-inhibitory concentration ($IC_{50}$) of 67 μmol/L to EBOV-Zaire type. The results of in vivo pharmacodynamics studies using the type I interferon receptor-deficient IFNAR−/−057BL/6 mouse model showed that at the challenge dose of 100% death of the placebo group, administered at a dose of 300 mg/kg/d from day 6 to day 13, Favipiravir showed a protection rate of 100%, and at the same time, the parameters such as body weight, glutamic-pyruvic transaminase, glutamic-oxalic transaminase, and viremia were also improved significantly. The relevant research results of the British Defense Science and Technology Laboratory showed that Favipiravir was not cytotoxic to Vero C1008 cells at a high concentration of 1.95 g/L, and could completely inhibit the cytopathic effect (CPE) of EBOV-Zaire type to cells at the drug concentration of above 62.5 mg/L. The A129 mouse models with both type I and type II interferon deficiencies were challenged at a dose of 100% death of the placebo group, and immediately intragastrically administered Favipiravir at dose of 300 mg/kg/d (2 times/d, 150 mg/kg per time) 1 h after the challenge for consecutive 14 days, which could protect 100% of the mice from death, and the body weight of the mice in the administration group had been significantly improved.

The 2019 novel Coronavirus (2019-nCoV) is a new coronavirus strain that has never been found in humans before. On Feb. 11, 2020, the International Committee on Taxonomy Viruses (ICTV) announced that the official name of 2019 novel Coronavirus (2019-nCoV) is severe acute respiratory syndrome coronavirus 2 (SARS-CoV-2). On the same day, the World Health Organization (WHO) announced that the official name of the disease caused by this virus is COVID-19. The symptoms of SARS-CoV-2 virus infection are mainly pneumonia, and can be divided into simple infection, mild pneumonia, severe pneumonia, acute respiratory distress syndrome, sepsis, septic shock and so on according to the severity of disease. Patients with simple infection may have non-specific symptoms, such as fever, cough, sore throat, nasal congestion, fatigue, headache, muscle pain or discomfort, and the elderly people and immunosuppressed people may have atypical symptoms. Patients with mild pneumonia mainly have cough, dyspnea and polypnea. Severe pneumonia can be seen in adolescents, adults or children, and the main symptoms of which include increased breathing frequency, severe respiratory failure or dyspnea, central cyanosis, drowsiness, unconsciousness or convulsion, gasp, etc. The lung images of acute respiratory distress syndrome are bilateral ground glass shadows, which cannot be completely explained by effusion, lobar exudation or atelectasis or lung mass shadows, and the main symptom of which is pulmonary edema. Patients with sepsis often have fatal organ dysfunction, and the most critical patients are those with septic shock, and they may have a high probability of death.

At present, the novel coronavirus infection is mainly treated with supportive therapy in clinic, and no specific antiviral drug is available.

CONTENTS OF THE APPLICATION

The purpose of the present application is to find a drug with antiviral activity against coronavirus, especially SARS coronavirus (SARS-CoV) and SARS-CoV-2, which can be used for the treatment of a related disease caused by the infection thereof, such as simple infection (such as fever, cough and sore throat), pneumonia, acute or severe acute respiratory tract infection, hypoxic respiratory failure and acute respiratory distress syndrome, sepsis and septic shock. Through creative research, it is found in the present application that Favipiravir represented by Formula I has the function of inhibiting the replication of SARS coronavirus (SARS-CoV) and SARS-CoV-2, and has a good potential therapeutic effect in the treatment of a disease caused by SARS coronavirus (SARS-CoV) or SARS-CoV-2.

The present application relates to a compound represented by Formula I, a geometric isomer, a pharmaceutically acceptable salt, a solvate and/or a hydrate thereof:

Formula I

In some embodiments, the pharmaceutically acceptable salts of the compound represented by Formula I described herein include inorganic or organic acid salts and inorganic or organic base salts thereof. The present application relates to all forms of the above salts, including but not limited to: sodium salt, potassium salt, calcium salt, lithium salt, meglumine salt, hydrochloride salt, hydrobromide salt, hydroiodide salt, nitrate salt, sulfate, hydrogen sulfate, phosphate, hydrogen phosphate, acetate, propionate, butyrate, oxalate, pivalate, adipate, alginate, lactate, citrate, tartrate, succinate, maleate, fumarate, picrate, aspartate, gluconate, benzoate, methanesulfonate, ethanesulfonate, benzenesulfonate, p-toluenesulfonate and embonate and so on.

The compound represented by Formula I can inhibit the replication of coronavirus in cells and reduce the nucleic acid load of coronavirus in cell culture.

After creative invention research, the inventors of the present application have discovered new features of the compound represented by Formula I in cells:

firstly, the compound represented by Formula I can reduce the viral nucleic acid load in cells infected by SARS-CoV-2 at micromolar concentration level;

secondly, the compound represented by Formula I has a significant protective effect on the mice infected by SARS coronavirus (SARS-CoV).

The present application also relates to use of the compound represented by Formula I, a geometric isomer, a pharmaceutically acceptable salt, a solvate and/or a hydrate thereof in manufacture of a medicament for treating a disease or an infection (including but not limited to respiratory diseases (e.g., simple infections (such as fever, cough and sore throat), pneumonia, acute respiratory infection, severe acute respiratory infection (SARI), hypoxic respiratory failure and acute respiratory distress syndrome, sepsis and septic shock, severe acute respiratory syndrome (SARS), etc.)) caused by a coronavirus, especially a SARS coronavirus (SARS-CoV) and/or a SARS-CoV-2,

I

The present application also relates to use of the compound represented by Formula I, a geometric isomer, a pharmaceutically acceptable salt, a solvate and/or a hydrate thereof in manufacture of a medicament as coronavirus inhibitor.

The present application also relates to use of the compound represented by Formula I, a geometric isomer, a pharmaceutically acceptable salt, a solvate and/or a hydrate thereof in manufacture of a medicament for inhibiting the replication or reproduction of coronavirus in a cell (e.g., a cell of mammal).

The present application also relates to a pharmaceutical composition, which comprises the compound represented by Formula I, a geometric isomer, a pharmaceutically acceptable salt, a solvate and/or a hydrate thereof, preferably, the pharmaceutical composition further comprises a pharmaceutically acceptable carrier or excipient. Specifically, the pharmaceutical composition is a solid preparation, an injection, an external preparation, a spray, a liquid preparation, or a compound preparation.

In some embodiments, the pharmaceutical composition comprises an effective amount of the compound represented by formula I, a geometric isomer, a pharmaceutically acceptable salt, a solvate and/or a hydrate thereof.

The present application also relates to use of the pharmaceutical composition comprising the compound represented by Formula I, a geometric isomer, a pharmaceutically acceptable salt, a solvate and/or a hydrate thereof or the compound represented by Formula I, a geometric isomer, a pharmaceutically acceptable salt, a solvate and/or a hydrate thereof in manufacture of a medicament for treating a respiratory system disease, including but not limited to simple infection (such as fever, cough and sore throat), pneumonia, acute respiratory infection, severe acute respiratory infection (SARI), hypoxic respiratory failure, acute respiratory distress syndrome, sepsis, septic shock, severe acute respiratory syndrome (SARS), etc.).

The present application also relates to a method for treating and/or preventing a disease in a mammal in need or a method for inhibiting the replication or reproduction of coronavirus in a mammal in need, the method comprises administering to the mammal in need a therapeutically and/or prophylactically effective amount of the pharmaceutical composition comprising the compound represented by Formula I, a geometric isomer, a pharmaceutically acceptable salt, a solvate and/or a hydrate thereof or the compound represented by Formula I, a geometric isomer, a pharmaceutically acceptable salt, a solvate and/or a hydrate thereof, wherein the disease includes a disease caused by a coronavirus.

In some embodiments, the disease caused by a coronavirus especially SARS coronavirus (SARS-CoV) and SARS-CoV-2 includes but is not limited to a respiratory system disease (e.g., simple infection (such as fever, cough and sore throat), pneumonia, acute respiratory infection, severe acute respiratory infection (SARI), hypoxic respiratory failure, acute respiratory distress syndrome, sepsis, septic shock, severe acute respiratory syndrome (SARS), etc.)).

The present application also relates to use of a pharmaceutical composition in manufacture of a medicament for treating a disease or an infection caused by a coronavirus, especially SARS coronavirus (SARS-CoV) and SARS-CoV-2 (e.g., a respiratory disease (e.g., simple infection (such as fever, cough and sore throat), pneumonia, acute respiratory infection, severe acute respiratory infection (SARI), hypoxic respiratory failure, acute respiratory distress syndrome, sepsis, septic shock, severe acute respiratory syndrome (SARS), etc.)), wherein the pharmaceutical composition comprises a compound represented by Formula I, a geometric isomer, a pharmaceutically acceptable salt, a solvate and/or a hydrate thereof, preferably, the pharmaceutical composition further comprises a pharmaceutically acceptable carrier or excipient. Specifically, the pharmaceutical composition is a solid preparation, an injection, an external preparation, a spray, a liquid preparation, or a compound preparation.

The present application also relates to use of a pharmaceutical composition in manufacture of a medicament as a coronavirus inhibitor, wherein the pharmaceutical composition comprises the compound represented by Formula I, a geometric isomer, a pharmaceutically acceptable salt, a solvate and/or a hydrate thereof, preferably, the pharmaceutical composition further comprises a pharmaceutically acceptable carrier or excipient. Specifically, the pharmaceutical composition is a solid preparation, an injection, an external preparation, a spray, a liquid preparation, or a compound preparation.

The present application also relates to use of a pharmaceutical composition in manufacture of a medicament for inhibiting the replication or reproduction of coronavirus in a cell (e.g., a cell of mammal), wherein the pharmaceutical composition comprises the compound represented by Formula I, a geometric isomer, a pharmaceutically acceptable salt, a solvate and/or a hydrate thereof, preferably, the pharmaceutical composition further comprises a pharmaceutically acceptable carrier or excipient. Specifically, the pharmaceutical composition is a solid preparation, an injection, an external preparation, a spray, a liquid preparation, or a compound preparation.

The present application also relates to the compound represented by Formula I, a geometric isomer, a pharmaceutically acceptable salt, a solvate and/or a hydrate thereof, for use in treating a disease or an infection caused by a coronavirus, especially SARS coronavirus (SARS-CoV) and SARS-CoV-2 (e.g., including but not limited to respiratory disease (e.g., simple infection (such as fever, cough and sore throat), pneumonia, acute respiratory infection, severe acute respiratory infection (SARI), hypoxic respiratory failure, acute respiratory distress syndrome, sepsis, septic shock, severe acute respiratory syndrome (SARS), etc.)).

The present application also relates to the compound represented by Formula I, a geometric isomer, a pharmaceutically acceptable salt, a solvate and/or a hydrate thereof, for use as a coronavirus inhibitor.

The present application also relates to the compound represented by Formula I, a geometric isomer, a pharmaceutically acceptable salt, a solvate and/or a hydrate thereof, for use in inhibiting the replication or reproduction of coronavirus in a cell (e.g., a cell of mammal).

The present application also relates to a pharmaceutical composition, for use in treating a disease or an infection caused by a coronavirus, especially SARS coronavirus (SARS-CoV) and SARS-CoV-2 (e.g., a respiratory system disease (e.g., simple infection (such as fever, cough and sore throat), pneumonia, acute respiratory infection, severe acute respiratory infection (SARI), hypoxic respiratory failure, acute respiratory distress syndrome, sepsis, septic shock, severe acute respiratory syndrome (SARS), etc.)), wherein the pharmaceutical composition comprises the compound represented by Formula I, a geometric isomer, a pharmaceutically acceptable salt, a solvate and/or a hydrate thereof, preferably, the pharmaceutical composition further comprises a pharmaceutically acceptable carrier or excipient. Specifically, the pharmaceutical composition is a solid preparation, an injection, an external preparation, a spray, a liquid preparation, or a compound preparation.

The present application also relates to a pharmaceutical composition, for use as a coronavirus inhibitor, wherein the pharmaceutical composition comprises the compound represented by Formula I, a geometric isomer, a pharmaceutically acceptable salt, a solvate and/or a hydrate thereof, preferably, the pharmaceutical composition further comprises a pharmaceutically acceptable carrier or excipient. Specifically, the pharmaceutical composition is a solid preparation, an injection, an external preparation, a spray, a liquid preparation, or a compound preparation.

The present application also relates to a pharmaceutical composition, for use in inhibiting the replication or reproduction of coronavirus in a cell (e.g., a cell of mammal), wherein the pharmaceutical composition comprises the compound represented by Formula I, a geometric isomer, a pharmaceutically acceptable salt, a solvate and/or a hydrate thereof, preferably, the pharmaceutical composition further comprises a pharmaceutically acceptable carrier or excipient. Specifically, the pharmaceutical composition is a solid preparation, an injection, an external preparation, a spray, a liquid preparation, or a compound preparation.

In some embodiments, the coronavirus in the present application is SARS coronavirus (SARS-CoV) or SARS-CoV-2.

In some embodiments, the coronavirus in the present application is SARS-CoV-2.

In some embodiments, the disease caused by a coronavirus in the present application is a disease caused by a SARS-CoV-2, namely COVID-19.

In some embodiments, the disease caused by a coronavirus in the present application is atypical pneumonia caused by a SARS coronavirus (SARS-CoV).

In some embodiments, the mammal in the present application includes bovine, equine, caprid, suidae, canine, feline, rodent, primate, for example, human, cat, dog or pig.

In the present application, the official name of the term "2019 novel Coronavirus (2019-nCoV)" is severe acute respiratory syndrome coronavirus 2 (SARS-CoV-2).

In the present application, the official name of the term "disease caused by 2019 novel coronavirus (2019-nCoV)" is COVID-19.

In the present application, the term "therapeutically effective amount" or "prophylactically effective amount" refers to an amount that is sufficient to treat or prevent a patient's disease but is sufficiently low to avoid serious side effects (at a reasonable benefit/risk ratio) within a reasonable medical judgment. The therapeutically effective amount of the compound will change according to the factors such as the selected specific compound (e.g., considering the efficacy, effectiveness, and half-life of compound), the selected administration route, the treated disease, the severity of the treated disease, the patient's age, size, weight and physical disease, medical history, duration of treatment, nature of concurrent therapy, desired therapeutic effect, etc., but can still be routinely determined by those skilled in the art.

In addition, it should be noted that the specific dosage and method of using the compound represented by Formula I, a geometric isomer, a pharmaceutically acceptable salt, a solvate and/or a hydrate thereof for different patients depends on many factors, including the patient's age, weight, gender, natural health status, nutritional status, active strength of drug, administration time, metabolic rate, severity of disease, and subjective judgment of physician. Herein it is preferred to use a dosage between 0.001-1000 mg/kg body weight/day.

The pharmaceutical composition described in the present application can be prepared into various forms according to different administration routes.

According to the present application, the pharmaceutical composition can be administered in any one of the following routes: oral administration, spray inhalation, rectal administration, nasal administration, buccal administration, vaginal administration, topical administration, parenteral administration such as subcutaneous, intravenous, intramuscular, intraperitoneal, intrathecal, intraventricular, intrasternal and intracranial injection or infusion, or administration with the help of an explant reservoir, wherein the preferred administration route is oral, intraperitoneal or intravenous administration.

When orally administered, the compound represented by Formula I, a geometric isomer, a pharmaceutically acceptable salt, a solvate and/or a hydrate thereof can be prepared into any form of orally acceptable preparation, including but not limited to a tablet, a capsule, an aqueous solution or an aqueous suspension. The carrier for use in a tablet generally includes lactose and corn starch, and a lubricant such as magnesium stearate can also be added. The diluent for use in a capsule generally includes lactose and dry corn starch. The aqueous suspension is usually used by mixing an active ingredient with a suitable emulsifier and a suitable suspending agent. If necessary, a sweetener, a flavoring agent or a coloring agent can also be added to the above-mentioned forms of oral preparation.

When rectally administered, the compound represented by Formula I, a geometric isomer, a pharmaceutically acceptable salt, a solvate, and/or a hydrate thereof can generally be prepared in a form of suppository, which is prepared by mixing the drug with a suitable non-irritating excipient. The excipient is present in solid state at room temperature, but melts at the rectal temperature to release the drug. Such excipient includes cocoa butter, beeswax and polyethylene glycol.

When topically administered, especially for treatment of easily accessible affected-surface or organ, such as eye, skin, or lower intestinal neurological disease by topical application, the compound represented by Formula I, a geometric isomer, a pharmaceutically acceptable salt, a solvate and/or a hydrate thereof can be prepared in various forms of topical preparations according to different affected-surfaces or organs, the specific instructions are as follows:

When topically administered to eye, the compound represented by Formula I, a geometric isomer, a pharmaceutically acceptable salt, a solvate and/or a hydrate thereof can be formulated into a preparation form such as micronized suspension or solution, the carrier used is isotonic sterile saline with a certain pH, and a preservative such as benzyl chloride alkoxide may or may not be added. In addition, for administration to eye, the compound can also be prepared in a form of ointment such as vaseline ointment.

When topically administered to skin, the compound represented by Formula I, a geometric isomer, a pharmaceutically acceptable salts, a solvate and/or a hydrate thereof can be prepared into a suitable form such as an ointment, a lotion or a cream, in which the active ingredient is suspended or dissolved in one or more carriers. The carrier for use in an ointment includes, but is not limited to: mineral oil, liquid petrolatum, white petrolatum, propylene glycol, polyethylene oxide, polypropylene oxide, emulsifying wax, and water. The carrier for use in a lotion or a cream includes, but is not limited to: mineral oil, sorbitan monostearate, Tween-60, cetyl ester wax, hexadecenyl aryl alcohol, 2-octyldodecanol, benzyl alcohol and water.

When topically administered to lower intestinal tract, the compound represented by Formula I, a geometric isomer, a pharmaceutically acceptable salt, a solvate and/or a hydrate thereof can be prepared into a form such as rectal suppository as described above or a suitable enema preparation form, in addition, a topical transdermal patch can also be used.

The compound represented by Formula I, a geometric isomer, a pharmaceutically acceptable salt, a solvate and/or a hydrate thereof can also be administered in a preparation form of sterile injection, including sterile injectable aqueous solution or oil suspension, or sterile injectable solutions, wherein the usable carrier and solvent includes water, Ringer's solution and isotonic sodium chloride solution. In addition, a sterilized non-volatile oil such as monoglyceride or diglyceride can also be used as solvent or suspension media.

The drugs of the above various preparation forms can be prepared according to conventional methods in the pharmaceutical field.

BRIEF DESCRIPTION OF THE DRAWINGS

In FIG. 1, (a) shows that Favipiravir can reduce the viral RNA load in the cells 48 h after the cells were infected by SARS-CoV-2, and the inhibitory activity is dose-dependent; in (a), the ordinate is the copy number of viral RNA in the sample, and the abscissa is the drug concentration; (b) shows that Favipiravir has no observable cytotoxicity 48 h after the cells are treated at the tested concentration; in (b), the ordinate is the percentage of cell viability relative to the vehicle control group (only cells, no drug added), and the abscissa is the drug concentration.

SPECIFIC MODELS FOR CARRYING OUT THE APPLICATION

The following examples are illustrative preferred embodiments of the present application and do not constitute any limitation to the present application.

Example 1: Experiment of Favipiravir in Reduction of Viral Nucleic Acid Load of Cells Infected by SARS-CoV-2

(1) Drug Treatment of Virus-Infected Cells

Vero E6 cells (purchased from ATCC, Catalog No. 1586) were placed into a 24-well plate and incubated for 24 hours, then virus infection was carried out, specifically, SARS-CoV-2 (2019-nCoV) virus (nCoV-2019BetaCoV/Wuhan/WIV04/2019 strain, provided by Wuhan Institute of Virology, Chinese Academy of Sciences) was diluted with 2% cell maintenance solution (formulation: FBS (purchased from Gibco, Catalog No.: 16000044) was added to MEM (purchased from Gibco, Article No: 10370021) by a volume ratio of 2%, thereby obtaining the 2% cell maintenance solution) to corresponding concentration, and then added to the 24-well plate so that each well contained a viral load of $100TCID_{50}$. Next, the Favipiravir (purchased from Selleck Chemicals, Catalog No.: 57975) was diluted with 2% cell maintenance solution to the corresponding concentrations and added to corresponding wells, so that the final drug concentrations were 100 µM, 33 µM, 11 µM, 3.7 µM, 1.23 µM, 0.14 µM, respectively, then the plate was put in 37° C., 5% $CO_2$ incubator and continuously cultured for 48 h, and the cell vehicle control group was added with only 2% cell maintenance solution without any test drug.

(2) RNA Extraction

The RNA extraction kit was purchased from Qiagen, Catalog No.: 74106. The consumptive materials (spin column, RNase-free 2 ml collection tube, etc.) and reagents (RLT, RW1, RPE, RNase-free water, etc.) involved in the following RNA extraction steps were all parts of the kit. The following extraction steps were all recommended by the kit instructions.

1) 100 µL of the supernatant was taken from the test plate, added to a nuclease-free EP tube, then added with 350 µL of Buffer RLT, mixed with a transfer liquid gun to make it fully lysed, and centrifuged to take the supernatant;

2) the supernatant obtained in step 1) was added with an equal volume of 70% ethanol and mixed well;

3) the mixed solution obtained in step 2) above was transferred to a RNase-free spin column, centrifuged at 12000 rpm for 15 s, and the waste liquid was discarded;

4) 700 µL of Buffer RW1 was added to the spin column, then centrifugation was carried out at 12000 rpm for 15 s to clean the spin column, and the waste liquid was discarded;

5) 500 µL of Buffer RPE was added to the spin column, then centrifugation was carried out at 12000 rpm for 15 s to clean the spin column, and the waste liquid was discarded;

6) 500 µL of Buffer RPE was added to the spin column, then centrifugation was carried out at 12000 rpm for 2 min to clean the spin column, and the waste liquid was discarded;

7) the spin column was placed in a new RNase-free 2 ml collection tube, and centrifugation was carried out at 12000 rpm for 1 min to dry the spin column, and then the entire spin column was transferred to the 1.5 ml collection tube of step 8);

8) the spin column dried in step 7) was placed in a new 1.5 ml collection tube, added with 30 µl of RNase-free water, and centrifuged at 12000 rpm for 2 min, the obtained eluent contained the corresponding RNA, and was added with RNase inhibitor (purchased from NEB, Catalog No.: M0314L), and detected with Nano Drop (purchased from Thermo scientific, Nano Drop One) to determine each RNA concentration.

(3) RNA Reverse Transcription

In the experiment, the reverse transcription kit (PrimeScript™ RT reagent Kit with gDNA Eraser, Catalog No. RR047Q) produced by TaKaRa Company was used for RNA reverse transcription. The steps were as follows.

① gDNA removal: RNA samples from each experimental group were collected, and 1 µg thereof was taken and subjected to reverse transcription. First, 2 µl of 5×gDNA Eraser Buffer was added to the RNA sample of each experimental group, the reaction system was supplemented with RNase Free water to 10 µl, mixed well, and subjected to 42° C. water bath for 2 min to remove the gDNA that might exist in the sample;

② Reverse transcription: the sample obtained in ① was added with appropriate amounts of enzyme, primer Mix and reaction buffer, supplemented with RNase Free water to an volume of 20 µl, reacted under 37° C. water bath for 15 min, then put in 85° C. water bath for 5 sec, thereby obtaining cDNA via transcription.

(4) Real-Time PCR

Fluorescence quantitative PCR was used to detect the copy number per ml of the original virus solution.

The reaction system was mixed using TB Green Premix (Takara, Cat #RR820A), and the amplification reaction and reading were carried out with StepOne Plus Real-time PCR instrument (brand: ABI). The copy number contained in per ml of the original virus solution was calculated. The steps were as follows:

① Establishment of standard product: the plasmid pMT-RBD (the plasmid was provided by Wuhan Institute of Virology, Chinese Academy of Sciences) was diluted to $5\times10^8$ copies/µL, $5\times10^7$ copies/µL, $5\times10^6$ copies/µL, $5\times10^5$ copies/µL, $5\times10^4$ copies/µL, $5\times10^3$ copies/µL, $5\times10^2$ copies/µL. 2 µL standard or cDNA template was taken for qPCR reaction.

② The sequences of primers used in the experiment were as follows (all indicated in 5'-3' direction):
RBD-qF: CAATGGTTTAACAGGCACAGG
RBD-qR: CTCAAGTGTCTGTGGATCACG ③ The reaction procedure was as follows:
Pre-denaturation: 95° C. for 5 minutes;
Cycle parameters: 95° C. for 15 seconds, 54° C. for 15 seconds, 72° C. for 30 seconds, for a total of 40 cycles.

(5) Cytotoxicity Test of Drug

The detection of the drug cytotoxicity was performed using CCK-8 kit (Beyotime). Specific steps were as follows:

① 1×10$^4$ Vero E6 (ATCC) cells were placed in a 96-well plate and incubated at 37° C. for 8 hours.

② The drug was diluted with DMSO to an appropriate concentration of mother liquor, and then diluted with MEM medium (purchased from Gibco, Catalog No. 10370021) containing 2% FBS (purchased from Gibco, Catalog No. 16000044) to the same concentration as that for the drug treatment. The original medium in the 96-well plate was discarded, 100 μL of drug-containing MEM medium was added to the cells, and three replicate wells were prepared for each concentration. Vehicle control (DMSO and medium were added to the cell wells, without adding drug) and blank control (DMSO and medium were added to the wells, without cells) were set up. After the drug was added, the cells were cultured at 37° C. for 48 hours.

③ 20 μL of CCK-8 solution (Beyotime) was added to the well to be tested, mixed gently, without generating bubbles, and continuously incubated at 37° C. for 2 hours. OD$_{450}$ was read on a microplate reader (purchased from Molecular Devices, Model: SpectraMax M5), and cell viability was calculated:

Cell activity (%)=($A_{(drug\ treatment\ group)}$−$A_{(blank\ control)}$)/($A_{(vehicle\ control)}$−$A_{(blank\ control)}$)×100% wherein A was the reading of the microplate reader.

(6) Experimental Results

Figure 1:
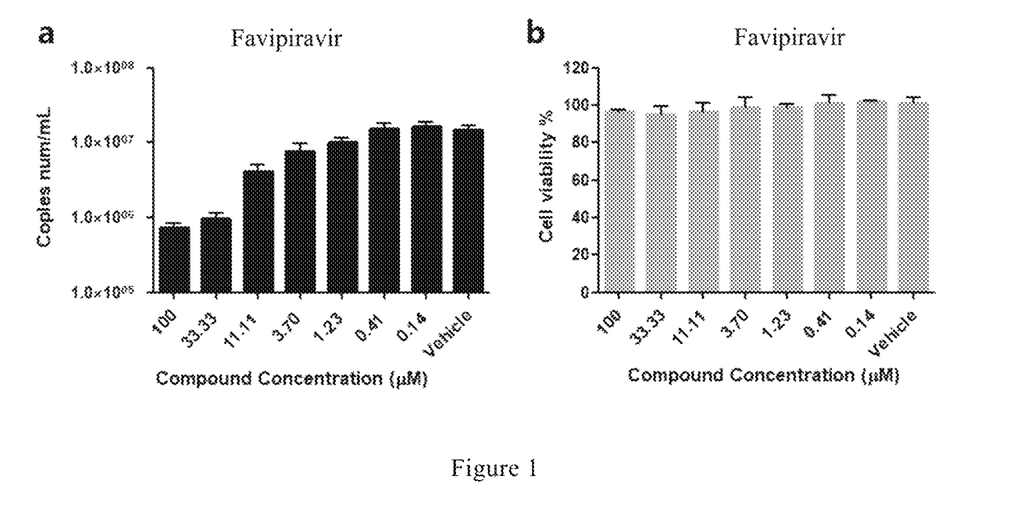
FIG. 1 shows that Favipiravir can effectively reduce the viral nucleic acid load in Vero E6 cells infected by SARS-CoV-2.
Figure 2:
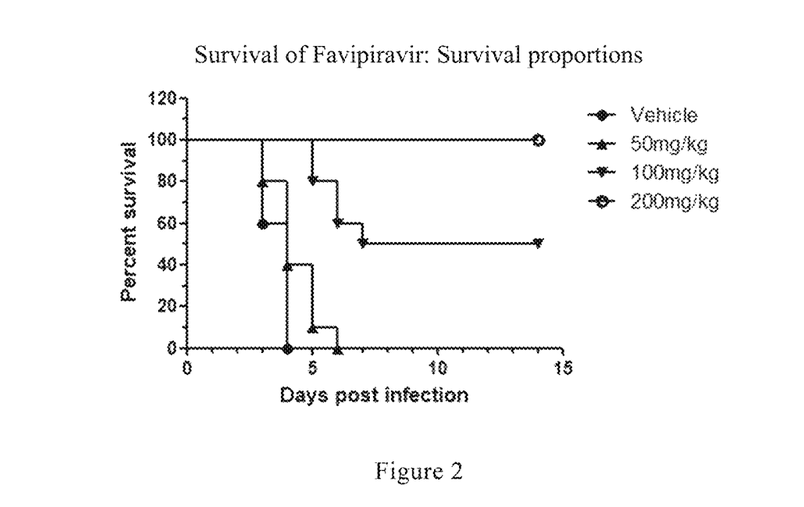
FIG. 2 shows that Favipiravir can effectively protect SARS coronavirus-infected mice from death. The mice were intraperitoneally injected with Favipiravir once a day 4 hours after challenge, and the vehicle control group was injected with the same volume of solvent. It can be seen that all mice of the vehicle control group died, while the mice of the Favipiravir treatment group survived, and the survival rate is dose-dependent.

The results of the virus proliferation inhibition experiment showed that the test compound at concentrations of 100 μM, 33 μM, 11.1 μM and 3.7 μM could effectively inhibit the replication of the SARS-CoV-2 virus genome in the infected supernatant (Table 1 and FIG. 1)

Example 2: Experiment of Favipiravir in Protecting SARS Coronavirus-Infected Mice from Death (1) Grouping and Marking of Mice A129 mice aged 3-4 weeks and weighed 9-13 g (provided by Institut Pasteur of Shanghai, Chinese Academy of Sciences) were randomly divided into 4 groups, namely the virus control group, the high-dose administration group, the middle-dose administration group and the low-dose administration group, 10 mice per group, marked with ear studs.

(2) Preparation of Drug 0.5% CMC-Na was used as solvent to dissolve Favipiravir. First, the drug Favipiravir was accurately weighed, added with an appropriate amount of 0.5% CMC-Na solution, alternately treated under vortex and ultrasonic condition for 15 min until the sample was a uniform particle suspension, then diluted with 0.5% CMC-Na by 2-fold, and the dilution was carried out according to administration dose of 200 mg/kg, 100 mg/kg and 50 mg/kg, respectively. The resultant drug solutions were stored at 4° C. for later use.

(3) Challenge to Mice, Dosing and Data Collection

The challenge was carried out by intraperitoneal injection, i.e., each mouse was intraperitoneally injected with SARS coronaviruses (provided by the Academy of Military Medicine) at a challenge dose of $1*10^6$ PFU, wherein the viruses were diluted with normal saline to the required dose. The intraperitoneal administration was carried out once 4 h, 24 h, 48 h, 72 h, 96 h, 120 h and 144 h after the challenge, respectively, in which the administration doses were high dose of 200 mg/kg, medium dose of 100 mg/kg and low dose of 50 mg/kg, and the virus control group was given the same volume of 0.5% CMC-Na solvent. The weighing and recording were carried out at fixed time points every day, the death of mice was recorded at the same time, and the survival curve was drawn, as shown in FIG. 2.

(4) Experimental Results

The results of in vivo experiments showed that the terminal survival rate of mice was in a dose-effect-dependent relationship with the dose (Table 3 and FIG. 2), indicating that the treatment with the test compound Favipiravir can effectively protect mice from SARS coronavirus infection-caused death.

TABLE 1

In vitro antiviral test of the test compound (Favipiravir)

| | Concentration (μM) | | | | | | | |
|---|---|---|---|---|---|---|---|---|
| | 100 | 33.33 | 11.11 | 3.70 | 1.23 | 0.41 | 0.14 | Vehicle |
| Virus genome copy number | 734518 ± 93620.94 | 977681.5 ± 168821.04 | 4062127 ± 962839.02 | 7774632.5 ± 2109225.28 | 10179836.5 ± 1557937.97 | 15541494.5 ± 2355070.75 | 16152218 ± 2720484.45 | 14672963 ± 2282738.68 |

The cytotoxicity test results showed that the treatment of the test compound (Favipiravir) did not change the cell viability at all test concentrations, that was, the test compound had no toxic effect on the cells at all test concentrations (Table 2 and FIG. 1).

TABLE 2

Cytotoxicity test results of the test compound (Favipiravir)

| | Concentration (μM) | | | | | | | |
|---|---|---|---|---|---|---|---|---|
| | 100 | 33.33 | 11.11 | 3.70 | 1.23 | 0.41 | 0.14 | Vehicle |
| Cell viability (% of vehicle control) | 96.37 ± 1.26 | 95.21 ± 4.43 | 96.42 ± 4.77 | 99.09 ± 4.91 | 98.57 ± 1.90 | 101.38 ± 3.85 | 101.61 ± 0.74 | 101.20 ± 3.08 |

TABLE 3

In vivo antiviral experiment results of test compound (Favipiravir)

| Administration dose | Death rate |
|---|---|
| Vehicle (solvent control) | 100% |
| 50 mg/kg | 100% |
| 100 mg/kg | 50% |
| 200 mg/kg | 0% |

What is claimed is:

1. A method for treating a disease in a mammal in need thereof, the method comprising administering to the mammal a therapeutically effective amount of (a) a pharmaceutical composition comprising a compound represented by Formula I, or a pharmaceutically acceptable salt thereof,

I or, (b) a compound represented by Formula I, or a pharmaceutically acceptable salt, thereof,
wherein the disease is a disease caused by severe acute respiratory syndrome coronavirus 2 (SARS-CoV-2).

2. The method according to claim 1, wherein the disease caused by SARS-CoV-2 is COVID-19.

3. The method according to claim 1, wherein the disease caused by SARS-CoV-2 is atypical pneumonia.

4. The method according to claim 1, wherein the disease caused by SARS-CoV-2 is a respiratory disease.

5. The method according to claim 1, wherein the disease caused by SARS-CoV-2 is simple infection, pneumonia, acute respiratory infection, severe acute respiratory infection (SARI), hypoxic respiratory failure, acute respiratory distress syndrome, sepsis, septic shock, or severe acute respiratory syndrome (SARS).

6. The method according to claim 5, wherein the simple infection is fever, cough and/or sore throat.

7. The method according to claim 1, wherein the mammal is a bovine, equine, caprid, suidae, canine, feline, rodent, or primate.

8. The method according to claim 7, wherein the mammal is a human, cat, dog, or pig.

9. A method for inhibiting the replication or reproduction of severe acute respiratory syndrome coronavirus 2 (SARS-CoV-2) in a mammal in need thereof, the method comprising administering to the mammal a therapeutically effective amount of (a) a pharmaceutical composition comprising a compound represented by Formula I, or a pharmaceutically acceptable salt thereof,

I or, (b) a compound represented by Formula I, or a pharmaceutically acceptable salt thereof,
wherein the mammal has a disease caused by SARS-CoV-2.

10. The method according to claim 9, wherein the disease caused by SARS-CoV-2 is COVID-19.

11. The method according to claim 9, wherein the disease caused by SARS-CoV-2 is atypical pneumonia.

12. The method according to claim 9, wherein the disease caused by SARS-CoV-2 is a respiratory disease.

13. The method according to claim 9, wherein the disease caused by SARS-CoV-2 is simple infection, pneumonia, acute respiratory infection, severe acute respiratory infection (SARI), hypoxic respiratory failure, acute respiratory distress syndrome, sepsis, septic shock, or severe acute respiratory syndrome (SARS).

14. The method according to claim 13, wherein the simple infection is fever, cough and/or sore throat.

15. The method according to claim 9, wherein the mammal is a bovine, equine, caprid, suidae, canine, feline, rodent, or primate.

16. The method according to claim 15, wherein the mammal is a human, cat, dog, or pig.

* * * * *